United States Patent
Fuhrman et al.

(10) Patent No.: US 6,675,799 B2
(45) Date of Patent: Jan. 13, 2004

(54) DEVICE AND METHOD OF ISOLATING BIAS FLOW

(75) Inventors: Bradley P. Fuhrman, Buffalo, NY (US); Mark S. Dowhy, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/199,655

(22) Filed: Jul. 19, 2002

(65) Prior Publication Data

US 2003/0015199 A1 Jan. 23, 2003

Related U.S. Application Data

(60) Provisional application No. 60/307,060, filed on Jul. 20, 2001, and provisional application No. 60/392,314, filed on Jun. 28, 2002.

(51) Int. Cl.[7] ............................................... A62B 7/00
(52) U.S. Cl. ........................... 128/205.15; 128/205.16; 128/205.12
(58) Field of Search ................. 128/202.26, 205.12, 128/205.14, 205.15, 205.16, 205.28

(56) References Cited

U.S. PATENT DOCUMENTS

| | | | |
|---|---|---|---|
| 3,396,723 A | * 8/1968 | Freytag | 128/205.14 |
| 4,354,536 A | * 10/1982 | Moss | 141/383 |
| 4,466,433 A | 8/1984 | Robbins | |
| 4,719,910 A | 1/1988 | Jensen | |
| 4,747,402 A | 5/1988 | Reese et al. | |
| 4,753,245 A | * 6/1988 | Gedeon | 600/531 |
| 4,805,612 A | 2/1989 | Jensen | |
| 4,821,709 A | 4/1989 | Jensen | |
| 4,879,996 A | 11/1989 | Harwood, Jr. et al. | |
| 4,951,659 A | * 8/1990 | Weiler et al. | 128/200.18 |
| 5,092,326 A | 3/1992 | Winn et al. | |
| 5,165,398 A | 11/1992 | Bird | |
| 5,299,579 A | * 4/1994 | Gedeon et al. | 600/532 |
| 5,307,794 A | 5/1994 | Rauterkus et al. | |
| 5,555,880 A | 9/1996 | Winter et al. | |
| 5,694,924 A | * 12/1997 | Cewers | 128/204.21 |
| 5,730,119 A | * 3/1998 | Lekholm | 128/200.24 |
| 5,850,835 A | 12/1998 | Takaki et al. | |

OTHER PUBLICATIONS

Lunkenbeimer, P.P., et al., "Intrapulmonaler Gaswechsel Unter Simulierter Apnoe Durch Transtrachealen, Periodischen Intrathorakalen Druckwechsel" Anacethetist 22, 232–238 (1973).

Ngeow, Y.K. and Mitzner, W., "A New System For Ventilating With High–Frequency Oscillation" J. Appl. Physiol.: Respirat. Environ. Exercise Physiol. 53(6): 1638–1642, 1982.

* cited by examiner

Primary Examiner—Aaron J. Lewis
(74) Attorney, Agent, or Firm—Hodgson Russ LLP

(57) ABSTRACT

An isolation device is disclosed. The isolation device may have a movable partition and a housing disposed about the movable partition. The isolation device may have a partition biaser joined to the partition, and a $CO_2$ scrubber. A method of delivering inspiratory gas to a patient is also disclosed.

67 Claims, 9 Drawing Sheets

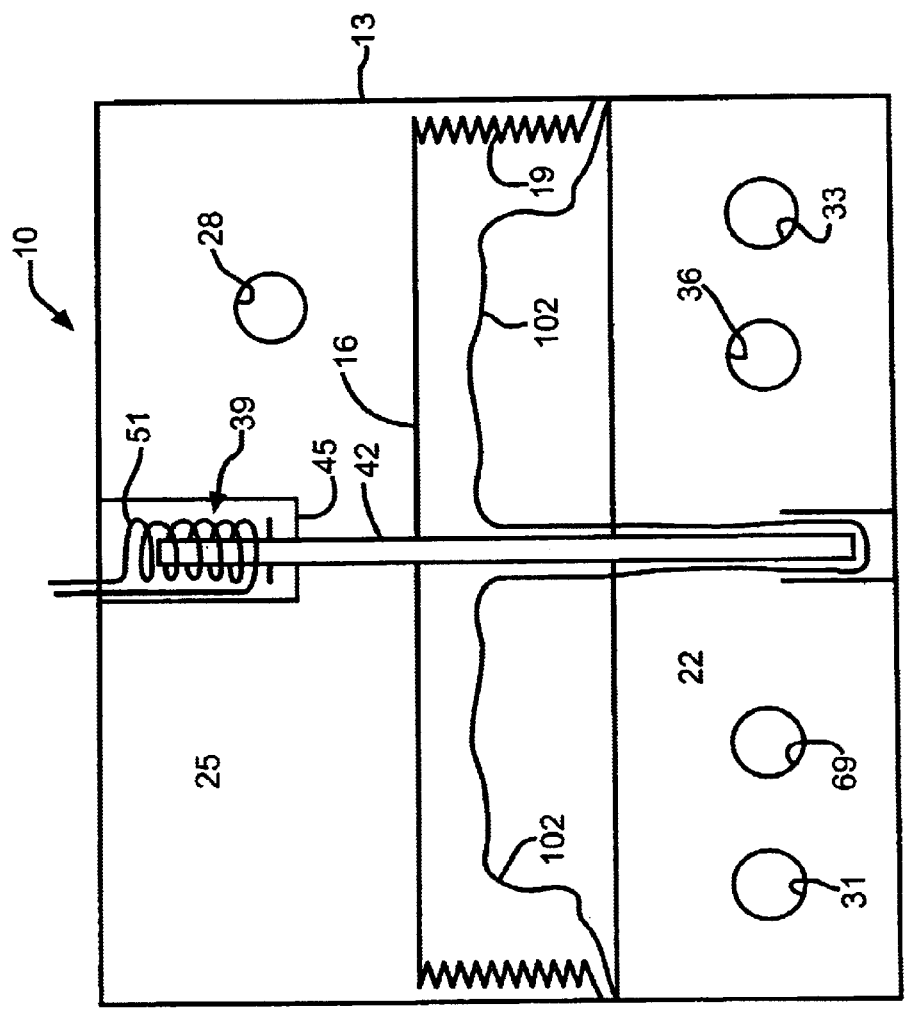

DEVICE AND METHOD OF ISOLATING BIAS FLOW

CLAIM OF PRIORITY

This application claims the benefit of U.S. patent application Ser. No. 60/307,060 filed on Jul. 20, 2001, and also claims the benefit of U.S. patent application Ser. No. 60/392,314 filed Jun. 28, 2002.

BACKGROUND INFORMATION

The invention relates generally to respirators, ventilators and oscillators used to deliver inspiratory gas to a patient. The term "respirator" is used herein to refer to respirators, ventilators and oscillators collectively. Rebreathing circuits, such as so called "circle circuits", are used in the operating rooms to conserve volatile anesthetics. There has been a move in the anesthesia field to low bias flow ("LBF") devices as a cost saving measure. While beneficial from an efficiency standpoint, some LBF devices are tedious for the clinician to use because they require manual adjustments of the bias flow to achieve the targeted inspiratory gas flow rate. New anesthesia machines have emerged to facilitate very low bias flows, and provide nearly closed circuit anesthesia. Examples of these LBF anesthesia machines are the Physioflex machine offered by Physio, Inc. and the machine described in U.S. Pat. No. 5,094,235. With these LBF anesthesia machines, the clinician sets the desired oxygen concentration and either the desired inspired or expired anesthetic agent concentration. These LBF anesthesia machines are not designed to allow precise control of the patient's ventilation using a refined ventilator like those used in intensive care facilities, while at the same time isolating the patient's breathing gas from that delivered by the ventilator.

BRIEF DESCRIPTION OF THE DRAWINGS

The nature and objects of the invention will be made clearer with reference to the following detailed description taken in conjunction with the accompanying drawings, in which:

FIGS. 3A and 3B are cross-sectional views of the isolation device shown in FIG. 2 taken along the line 3—3;

DETAILED DESCRIPTION

Figure 1:
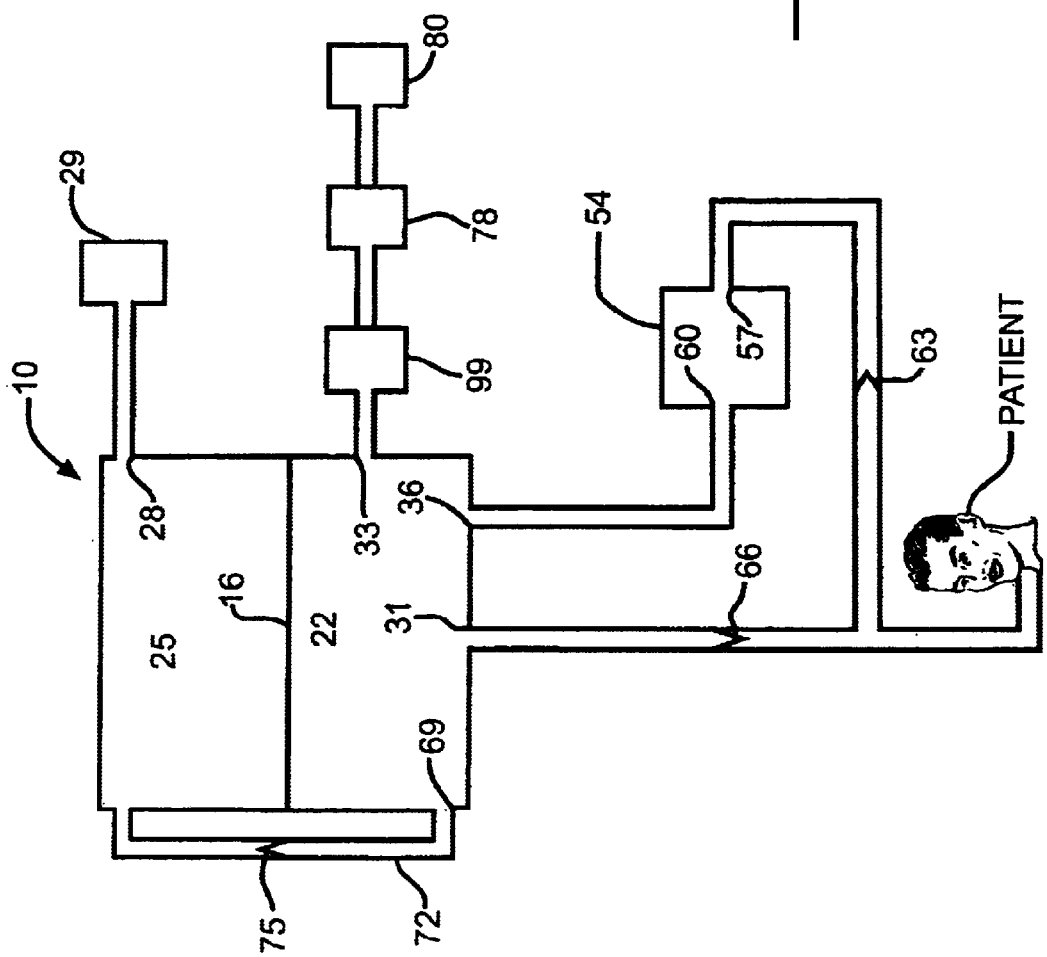
FIG. 1 is a schematic of a device according to the invention.
Figure 2:
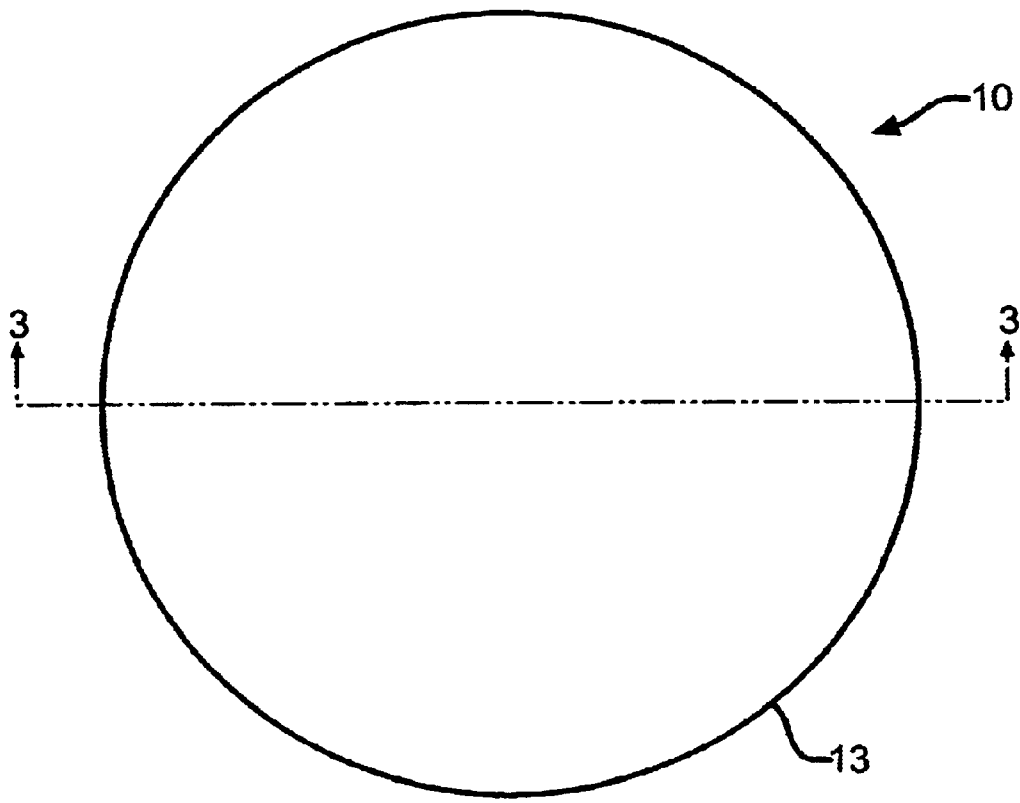
FIG. 2 is a top view of an isolation device according to the invention.

FIGS. 1, 2, 3A and 3B illustrate aspects of an isolation device 10 according to the present invention. The isolation device 10 may have a housing 13 disposed about a movable partition 16. The partition 16 may include an accordion sleeve 19 joined to the housing 13 to allow movement of the partition 16. The partition 16 may be joined to the housing 13 to separate a patient side 22 of the housing 13 from a respirator side 25 of the housing. The housing 13 also may have a respirator orifice 28 on the respirator side 25 that is adaptable to be in pneumatic communication with a respirator 29, and a patient inspiration orifice 31 on the patient side 22 that is adaptable to be in pneumatic communication with a patient. The housing 13 may have a bias inflow orifice 33 on the patient side 22 that is adaptable to be in pneumatic communication with a source of inspiratory gas, and an expiration return orifice 36 on the patient side 22. The housing 13 may be made of more than one piece, for example, the patient side 22 may be one piece and the respirator side 25 may be another piece.

An isolation device 10 according to the invention may have a partition biaser 39 joined to the partition 16. The partition biaser 39 may be operable to bias the partition 16 to an undisplaced position during an expiration period. One such partition biaser 39 may have a movable rod 42 joined to the partition 16, and a spring 48 joined to the rod 42 to provide a force that biases the partition 16 to the undisplaced position. A solenoid 51 may also be used to provide the bias force, and the solenoid 51 may be magnetically coupled to the rod 42. An abutment 45 may be provided to limit the travel of the rod 42, and therefore the partition 16.

An isolation device 10 according to the invention may have a $CO_2$ scrubber 54 having an inlet 57 in pneumatic communication with the patient and an outlet 60 in pneumatic communication with the expiration return orifice 36. A check valve 63 may be provided in pneumatic communication with the scrubber 54 to prevent gas from traveling from the scrubber 54 toward the patient and to permit exhaled gas from the patient to flow through the scrubber 54. A check valve 66 may be provided in pneumatic communication with the patient inspiration orifice 31 to encourage exhaled gas from the patient to flow through the scrubber 54 and to permit gas from the patient inspiration orifice 31 to flow to the patient.

In an embodiment of an isolation device 10 according to the invention, the housing 13 may have a bias release orifice 69 on the patient side 22, a bypass line 72 joined to the bias release orifice 69 and to the respirator side 25, and a release valve 75. The release valve 75 may be operable to allow gas to flow from the bias release orifice 69 to the respirator side 25 via the bypass line 72, for example by opening a gate in the release valve 75. The release valve 75 may also serve to prevent gas from flowing from the respirator side 25 to the bias release orifice 69. The release valve 75 may be operable to allow gas to flow from the bias release orifice 69 to the respirator side 25 when a pressure on the patient side 22 exceeds a pressure on the respirator side 25. The release valve 75 may be operable to allow gas to flow from the bias release orifice 69 to the respirator side 25 during an expiration period.

Figure 4A:
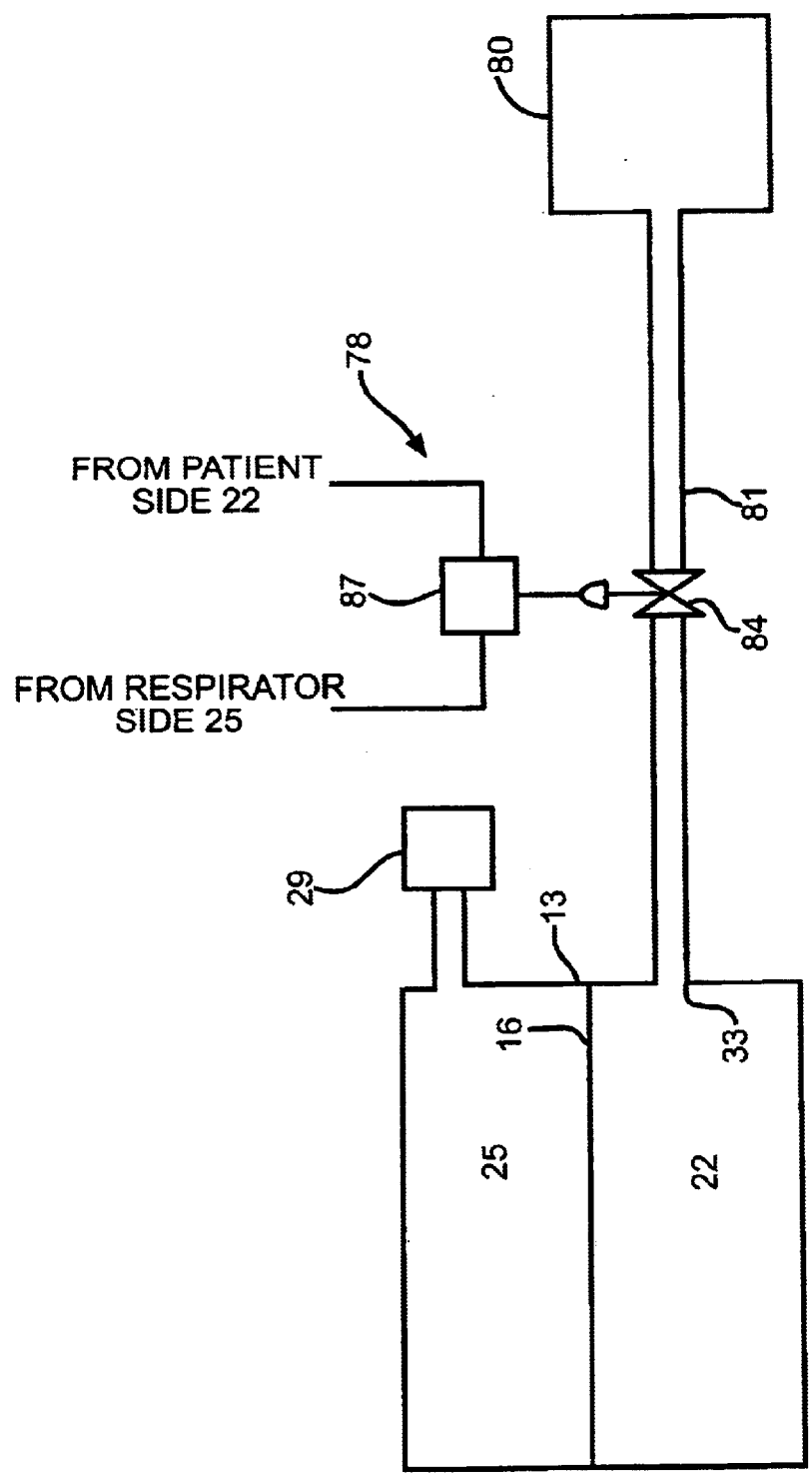
FIG. 4A is a schematic drawing of a controller according to the invention.
Figure 4B:
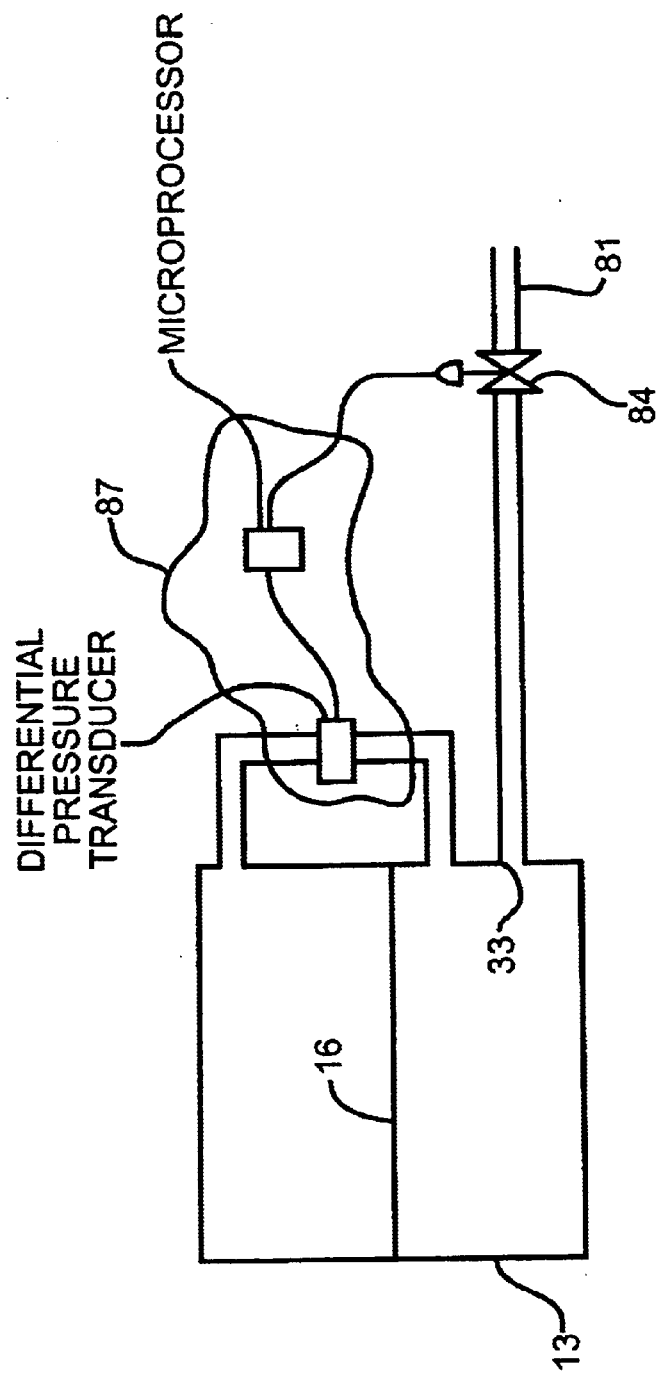
FIG. 4B shows an embodiment of the controller depicted in FIG. 4A.

A controller 78 may be provided that is operable to regulate a flow of gas from an inspiratory gas source 80 to the bias inflow orifice 33. The controller 78 may be operable to achieve a desired flow rate for the flow of gas to the bias inflow orifice 33. FIG. 4A illustrates aspects of a controller according to the invention. The controller 78 may regulate the flow of gas to the bias inflow orifice 33 based on a pressure difference between the respirator side 25 and the patient side 22. The controller 78 may include a bias flow line 81 in pneumatic communication with the bias inflow orifice 33, and a bias flow control valve 84 in the bias flow line 81. The controller 78 may include a pressure transducer 87 operable to provide a signal corresponding to a pressure difference between the respirator side 25 and the patient side 22, and wherein the bias flow control valve 84 is positionable according to the signal. FIG. 4B illustrates an embodiment of the controller depicted in FIG. 4A.

Figure 5A:
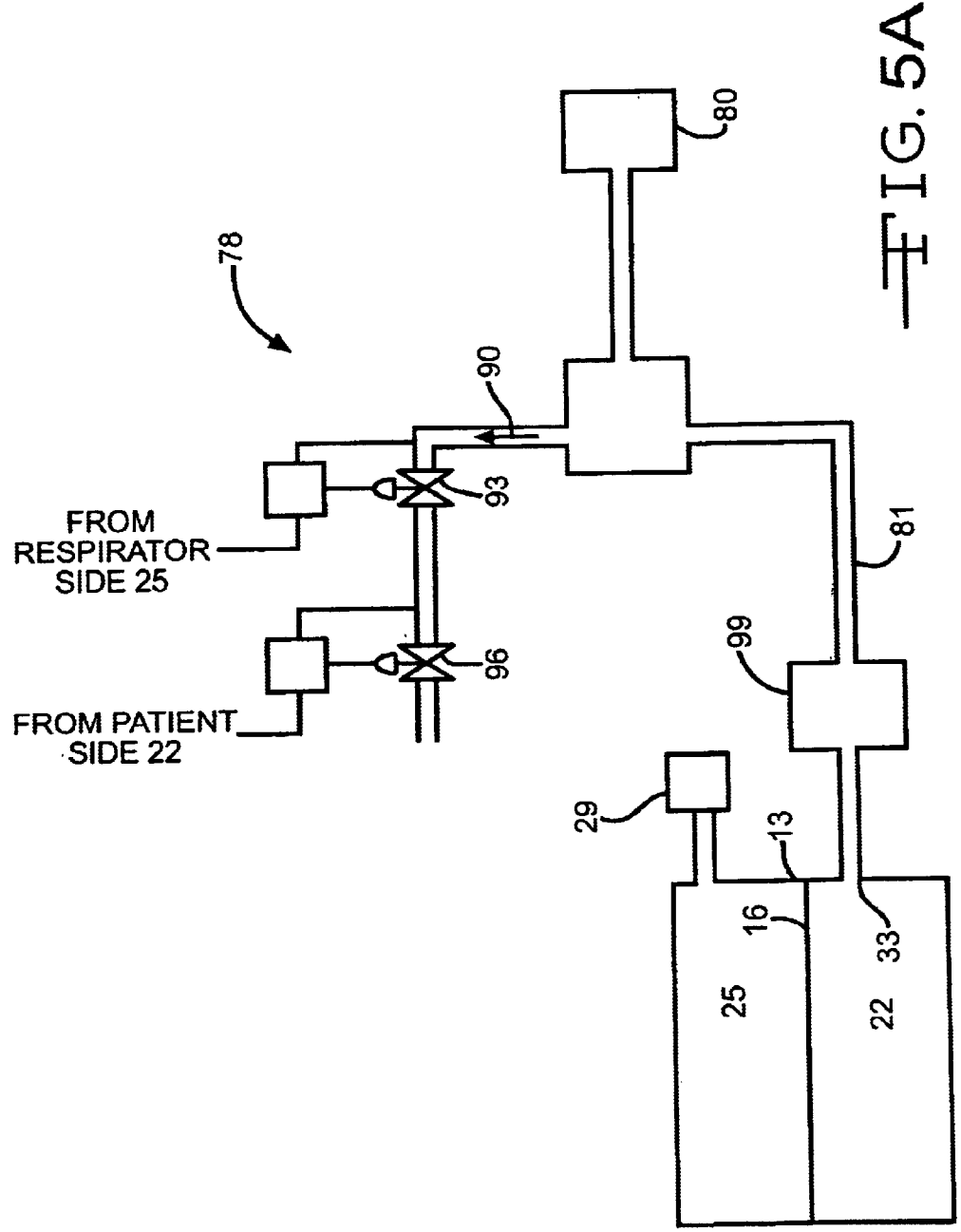
FIG. 5A is a schematic drawing of a controller according to the invention.
Figure 5B:
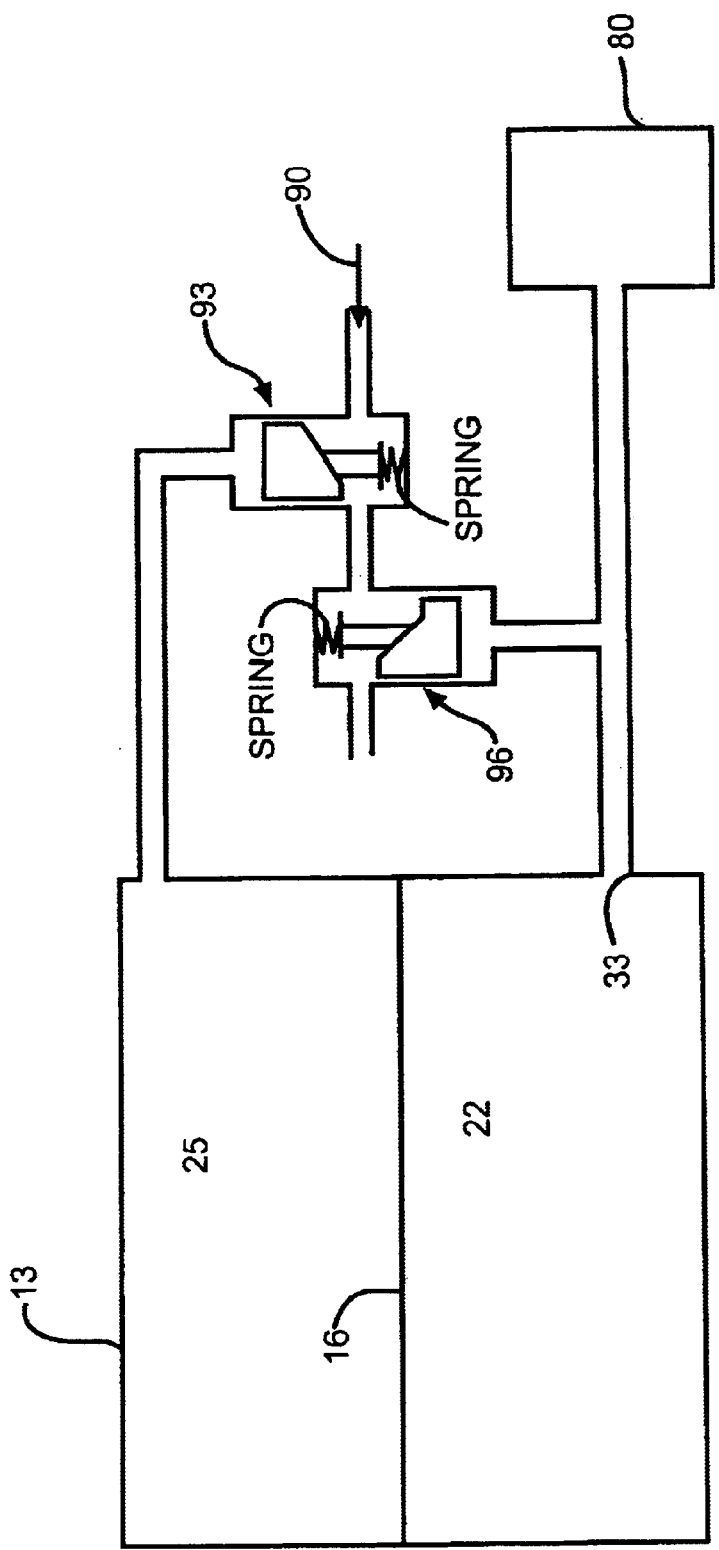
FIG. 5B shows an embodiment of the controller depicted in FIG. 5A.

FIG. 5A illustrates aspects of a controller 78 according to the invention that may divide a source flow of gas into the flow of gas to the bias inflow orifice 33 and a flow of waste gas indicated by arrow 90. The controller 78 may include one or more waste gas control valves 93, 96 that are operable to control the flow of waste gas 90. One such waste gas control valve 93 may be operable to inhibit the flow of waste gas 90 if a pressure difference between the respirator side 25 and the waste gas 90 is not within a range of acceptable pressures. One such waste gas control valve 96 may be operable to inhibit the flow of waste gas 90 if a pressure difference between the patient side 22 and the waste gas 90 is not within a range of acceptable pressures. FIG. 5B illustrates an embodiment of the controller depicted in FIG. 5A wherein the waste gas control valves 93, 96 do not include electrical components.

The bias inflow orifice 33 may be used to supply inspiratory gas from the inspiratory gas source 80 to the patient side 22 of the housing 13. A vaporizer, blender, mixer and/or nebulizer (shown as 99 in FIGS. 1 and 5A) may be placed in pneumatic communication with the bias inflow orifice 33, and these may be used to provide a therapeutic agent in the inspiratory gas.

Figure 3A:
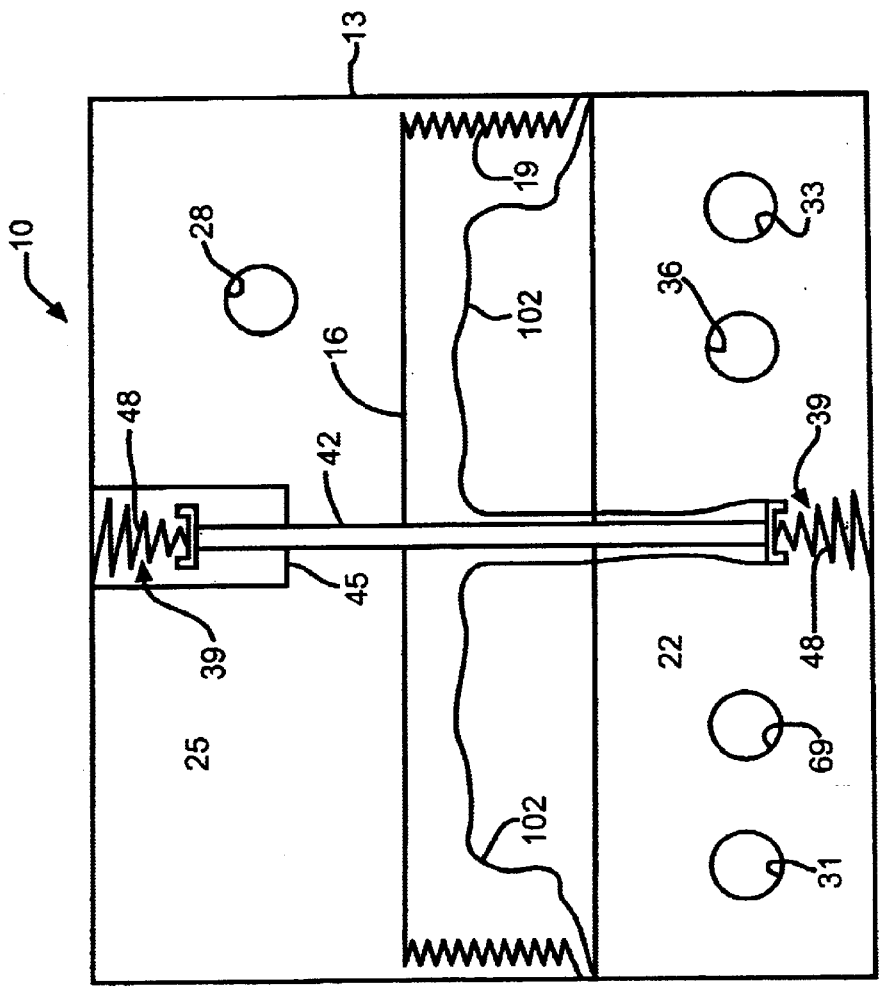

FIGS. 3A and 3B show a removable liner 102 that may be provided in the patient side 22 of the housing 13. The liner 102 may serve to keep exhaled material from contacting, and thus contaminating, the partition 16. In this manner, the liner 102 and patient side 22 of the housing 13 may be removed after a first patient is finished with the isolation device 10, and then remaining portions of the isolation device 10 may be used with a second patient.

Figure 6:
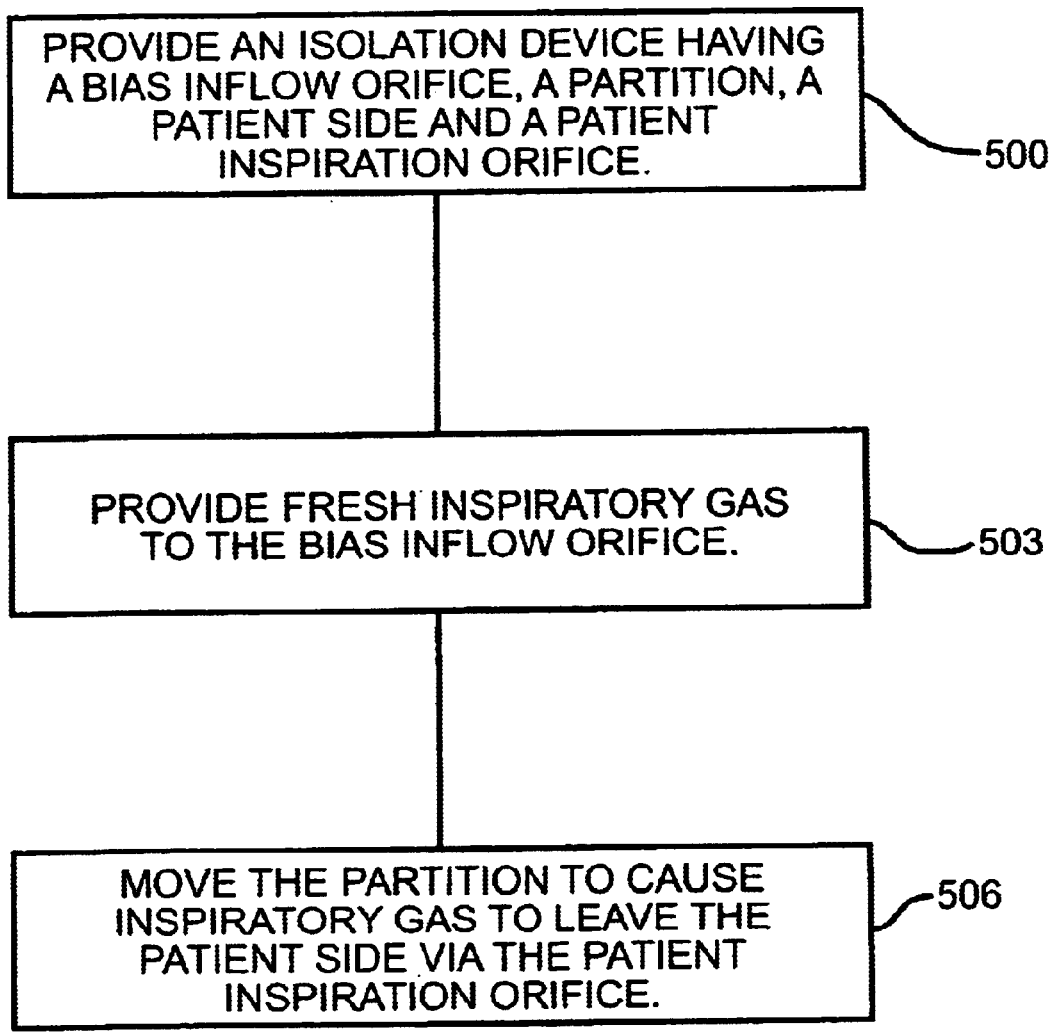
FIG. 6 is a flow chart of a method according to the invention.

FIG. 6 shows a method according to the invention. A method according to the invention may include delivering inspiratory gas to a respiratory system of a patient by providing 500 an isolation device, such as described above, providing 503 fresh inspiratory gas, which may include a therapeutic agent, to the bias inflow orifice, and moving 506 the partition to cause the inspiratory gas to leave the patient side via the patient inspiration orifice.

Moving the partition may be effected by increasing a pressure in the respirator side. A respirator may be provided in pneumatic communication with the respirator orifice, and the respirator may be used to increase the pressure in the respirator side during inspiration.

The partition may also be moved, for example, by the partition biaser. In one method according to the invention, the partition is moved by the partition biaser prior to increasing the pressure with the respirator, so that the partition seeks an undisplaced position during expiration. This may cause gas to move from the patient side to the respirator side via the bypass line, or it may create a pressure difference between the respirator side and the patient side that results in an increase in bias inflow to the patient side.

A method according to the invention may include moving the partition to allow expired gas from the patient to flow through the scrubber toward the expiration return orifice. This may be effected by decreasing a pressure on the respirator side. A respirator may be provided in pneumatic communication with the respirator orifice to decrease the pressure in the respirator side during expiration.

A method according to the invention may include providing a bypass line joined to the bias release orifice and the respirator side, and a release valve operable to allow gas to flow from the bias release orifice to the respirator side via the bypass line, and to prevent gas from flowing from the respirator side to the bias release orifice, and the method further comprises opening the release valve to reduce a pressure on the patient side.

Although the invention has been described with respect to one or more particular embodiments, it will be understood that other embodiments of the invention may be made without departing from the spirit and scope of the invention.

What is claimed is:

1. An isolation device, comprising:
   a movable partition;
   a housing disposed about the movable partition, the housing having a respirator side on a first side of the partition, and having a patient side on a second side of the partition, and having (a) a respirator orifice on the respirator side, adaptable to be in pneumatic communication with a respirator, (b) a patient inspiration orifice on the patient side, adaptable to be in pneumatic communication with a patient, (c) a bias inflow orifice on the patient side, adaptable to be in pneumatic communication with a source of inspiratory gas, and (d) an expiration return orifice on the patient side;
   a partition biaser joined to the partition;
   a $CO_2$ scrubber having an inlet in pneumatic communication with the patient and an outlet in pneumatic communication with the expiration return orifice; and
   a controller operable to regulate a flow of gas to the bias inflow orifice based on a pressure difference between the respirator side and the patient side.

2. The isolation device of claim 1, wherein the partition biaser is operable to bias the partition to an undisplaced position.

3. The isolation device of claim 1, wherein the partition biaser includes a movable rod joined to the partition.

4. The isolation device of claim 3, further comprising an abutment limiting movement of the rod.

5. The isolation device of claim 1, wherein the partition biaser includes a spring.

6. The isolation device of claim 5, further comprising a movable rod joined to the spring and the partition.

7. The isolation device of claim 1, wherein the partition biaser includes a solenoid.

8. The isolation device of claim 7, further comprising a movable rod magnetically coupled to the solenoid, and joined to the partition.

9. The isolation device of claim 1, further comprising a check valve in pneumatic communication with the scrubber to prevent gas from traveling from the scrubber toward the patient and to permit exhaled gas from the patient to flow through the scrubber.

10. The isolation device of claim 1, further comprising a check valve in pneumatic communication with the patient inspiration orifice to encourage exhaled gas from the patient to flow through the scrubber and to permit gas from the patient inspiration orifice to flow to the patient.

11. The isolation device of claim 1, wherein the housing further comprises a bias release orifice on the patient side, and the isolation device further comprises:
    a bypass line joined to the bias release orifice and the respirator side; and
    a release valve operable to allow gas to flow from the bias release orifice to the respirator side via the bypass line, and to prevent gas from flowing from the respirator side to the bias release orifice.

12. The isolation device of claim 11, wherein the release valve is operable to allow gas to flow from the bias release orifice to the respirator side when a pressure on the patient side exceeds a pressure on the respirator side.

13. The isolation device of claim 11, wherein the release valve is operable to allow gas to flow from the bias release orifice to the respirator side during an expiration period.

14. The isolation device of claim 1, wherein the controller is operable to achieve a desired flow rate for the flow of gas to the bias inflow orifice.

15. The isolation device of claim 1, wherein the controller includes a bias flow line in pneumatic communication with the bias inflow orifice, and a bias flow control valve in the bias flow line.

16. The isolation device of claim 15, wherein the controller includes a pressure transducer operable to provide a signal corresponding to a pressure difference between the respirator side and the patient side, and wherein the bias flow control valve is positionable according to the signal.

17. The isolation device of claim 1, wherein the controller divides a source flow of gas into the flow of gas to the bias inflow orifice and a flow of waste gas.

18. The isolation device of claim 17, wherein the controller includes a waste gas control valve operable to control the flow of waste gas.

19. The isolation device of claim 18, wherein the waste gas control valve inhibits the flow of waste gas if a pressure difference between the respirator side and the waste gas is not within a range of acceptable pressures.

20. The isolation device of claim 18, wherein the waste gas control valve inhibits the flow of waste gas if a pressure difference between the patient side and the waste gas is not within a range of acceptable pressures.

21. The isolation device of claim 17, wherein the controller includes a first waste gas control valve and a second waste gas control valve, the first waste gas control valve being operable to control the flow of waste gas by inhibiting the flow of waste gas if a pressure difference between the respirator side and the waste gas is not within a range of acceptable pressures, and the second waste gas control valve being operable to control the flow of waste gas by inhibiting the flow of waste gas if a pressure difference between the patient side and the waste gas is not within a range of acceptable pressures.

22. The isolation device of claim 1, wherein the bias inflow orifice is also in pneumatic communication with a vaporizer.

23. The isolation device of claim 1, wherein the bias inflow orifice is also in pneumatic communication with a blender.

24. The isolation device of claim 1, wherein the bias inflow orifice is also in pneumatic communication with a mixer.

25. The isolation device of claim 1, wherein the bias inflow orifice is also in pneumatic communication with a nebulizer.

26. The isolation device of claim 1, further comprising a removable liner disposed within the patient side.

27. The isolation device of claim 1, wherein the partition includes an accordion sleeve joined to the housing.

28. An isolation device, comprising:
a movable partition;
a housing disposed about the movable partition, the housing having a respirator side on a first side of the partition, and having a patient side on a second side of the partition, and having (a) a respirator orifice on the respirator side, adaptable to be in pneumatic communication with a respirator, (b) a patient inspiration orifice on the patient side, adaptable to be in pneumatic communication with a patient, (c) a bias inflow orifice on the patient side, adaptable to be in pneumatic communication with a source of inspiratory gas, (d) an expiration return orifice on the patient side, and (e) a bias release orifice on the patient side;
a bypass line joined to the bias release orifice and the respirator side;
a release valve operable to allow gas to flow from the bias release orifice to the respirator side via the bypass line, and to prevent gas from flowing from the respirator side to the bias release orifice;
a partition biaser joined to the partition; and
a $CO_2$ scrubber having an inlet in pneumatic communication with the patient and an outlet in pneumatic communication with the expiration return orifice.

29. The isolation device of claim 28, wherein the partition biaser is operable to bias the partition to an undisplaced position.

30. The isolation device of claim 28, wherein the partition biaser includes a movable rod joined to the partition.

31. The isolation device of claim 30, further comprising an abutment limiting movement of the rod.

32. The isolation device of claim 28, wherein the partition biaser includes a spring.

33. The isolation device of claim 32, further comprising a movable rod joined to the spring and the partition.

34. The isolation device of claim 28, wherein the partition biaser includes a solenoid.

35. The isolation device of claim 34, further comprising a movable rod magnetically coupled to the solenoid, and joined to the partition.

36. The isolation device of claim 28, further comprising a check valve in pneumatic communication with the scrubber to prevent gas from traveling from the scrubber toward the patient and to permit exhaled gas from the patient to flow through the scrubber.

37. The isolation device of claim 28, further comprising a check valve in pneumatic communication with the patient inspiration orifice to encourage exhaled gas from the patient to flow through the scrubber and to permit gas from the patient inspiration orifice to flow to the patient.

38. The isolation device of claim 28, wherein the release valve is operable to allow gas to flow from the bias release orifice to the respirator side when a pressure on the patient side exceeds a pressure on the respirator side.

39. The isolation device of claim 28, wherein the release valve is operable to allow gas to flow from the bias release orifice to the respirator side during an expiration period.

40. The isolation device of claim 28, further comprising a controller operable to regulate a flow of gas to the bias inflow orifice.

41. The isolation device of claim 40, wherein the controller is operable to achieve a desired flow rate for the flow of gas to the bias inflow orifice.

42. The isolation device of claim 40, wherein the controller regulates the flow of gas to the bias flow orifice based on a pressure difference between the respirator side and the patient side.

43. The isolation device of claim 40, wherein the controller includes a bias flow line in pneumatic communication with the bias inflow orifice, and a bias flow control valve in the bias flow line.

44. The isolation device of claim 43, wherein the controller includes a pressure transducer operable to provide a signal corresponding to a pressure difference between the respirator side and the patient side, and wherein the bias flow control valve is positionable according to the signal.

45. The isolation device of claim 40, wherein the controller divides a source flow of gas into the flow of gas to the bias inflow orifice and a flow of waste gas.

46. The isolation device of claim 45, wherein the controller includes a waste gas control valve operable to control the flow of waste gas.

47. The isolation device of claim 46, wherein the waste gas control valve inhibits the flow of waste gas if a pressure difference between the respirator side and the waste gas is not within a range of acceptable pressures.

48. The isolation device of claim 46, wherein the waste gas control valve inhibits the flow of waste gas if a pressure difference between the patient side and the waste gas is not within a range of acceptable pressures.

49. The isolation device of claim 45, wherein the controller includes a first waste gas control valve and a second waste gas control valve, the first waste gas control valve being operable to control the flow of waste gas by inhibiting the flow of waste gas if a pressure difference between the respirator side and the waste gas is not within a range of acceptable pressures, and the second waste gas control valve being operable to control the flow of waste gas by inhibiting the flow of waste gas if a pressure difference between the patient side and the waste gas is not within a range of acceptable pressures.

50. The isolation device of claim 28, wherein the bias inflow orifice is also in pneumatic communication with a vaporizer.

51. The isolation device of claim 28, wherein the bias inflow orifice is also in pneumatic communication with a blender.

52. The isolation device of claim 28, wherein the bias inflow orifice is also in pneumatic communication with a mixer.

53. The isolation device of claim 28, wherein the bias inflow orifice is also in pneumatic communication with a nebulizer.

54. The isolation device of claim 28, further comprising a removable liner disposed within the patient side.

55. The isolation device of claim 28, wherein the partition includes an accordion sleeve joined to the housing.

56. A method of delivering a inspiratory gas to a respiratory system of a patient, comprising:
providing an isolation device having (a) a movable partition, (b) a housing disposed about the movable partition, the housing having (i) a respirator side on a first side of the partition (ii) a patient side on a second side of the partition, (iii) a respirator orifice on the respirator side, adaptable to be in pneumatic communication with a respirator, (iv) a patient inspiration orifice on the patient side, adaptable to be in pneumatic communication with a patient, (v) a bias inflow orifice on the patient side, adaptable to be in pneumatic communication with a source of inspiratory gas, (vi) an expiration return orifice on the patient side, and (vii) a bias release orifice on the patient side, (c) a partition biaser joined to the partition, and (d) a $CO_2$ scrubber having an inlet in pneumatic communication with the patient and an outlet in pneumatic communication with the expiration return orifice;
providing an inspiratory gas to the bias inflow orifice;
moving the partition to cause the inspiratory gas to leave the patient side via the patient inspiration orifice.

57. The method of claim 56, wherein moving the partition is effected by increasing a pressure in the respirator side.

58. The method of claim 57, further comprising providing a respirator in pneumatic communication with the respirator orifice, the respirator increasing the pressure in the respirator side during inspiration.

59. The method of claim 58, further comprising moving the partition with the partition biaser prior to increasing the pressure with the respirator.

60. The method of claim 56, further comprising moving the partition to allow expired gas from the patient to flow through the scrubber toward the expiration return orifice.

61. The method of claim 60, wherein moving the partition to allow expired gas from the patient to flow through the scrubber toward the expiration return orifice is effected by decreasing a pressure on the respirator side.

62. The method of claim 61, further comprising providing a respirator in pneumatic communication with the respirator orifice, the respirator decreasing the pressure in the respirator side during expiration.

63. The method of claim 56, wherein the isolation device further comprises a bypass line joined to the bias release orifice and the respirator side, and a release valve operable to allow gas to flow from the bias release orifice to the respirator side via the bypass line, and to prevent gas from flowing from the respirator side to the bias release orifice, and the method further comprises opening the release valve to reduce a pressure on the patient side.

64. The method of claim 56, wherein the inspiratory gas includes a therapeutic agent.

65. The method of claim 56, further comprising applying a force to the partition via the partition biaser so as to produce a pressure difference between the patient side and the respirator side, the force being proportional to the displacement of the partition.

66. The method of claim 65, further comprising using the pressure difference to regulate bias release flow and bias inflow.

67. The method of claim 56, wherein the isolation device also has a bias inflow controller, and the method includes using the bias inflow controller to alter the flow of gas via the bias inflow orifice in response to a pressure difference between the patient side and the respirator side.

* * * * *